United States Patent [19]

Kuwata

[11] 4,275,439
[45] Jun. 23, 1981

[54] PROCESS CONTROL SYSTEM
[75] Inventor: Ryuichi Kuwata, Hachioji, Japan
[73] Assignee: Tokyo Shibaura Denki Kabushiki Kaisha, Kawasaki, Japan
[21] Appl. No.: 3,425
[22] Filed: Jan. 9, 1979
[30] Foreign Application Priority Data
   Jan. 24, 1978 [JP] Japan .................................. 53-5765
[51] Int. Cl.³ ....................... G05B 11/16; G06F 15/46
[52] U.S. Cl. .................................... 364/120; 318/561;
                                   318/610; 364/103; 364/105
[58] Field of Search ............... 364/120, 117, 105, 106,
       364/118, 103; 318/610, 561, 616, 617, 621, 490,
                                       596, 599, 672; 340/722

[56]         References Cited
       U.S. PATENT DOCUMENTS

| 2,866,108 | 12/1958 | Olsen et al. ....................... 318/610 X |
| 3,422,418 | 1/1969 | Simoneau .............................. 364/120 |
| 3,882,368 | 5/1975 | Carleton ............................... 318/610 |
| 3,947,665 | 3/1976 | Hundley ............................... 364/120 |
| 3,987,351 | 10/1976 | Appelberg et al. ............. 364/120 X |
| 4,064,394 | 12/1977 | Allen ................................ 364/103 X |

FOREIGN PATENT DOCUMENTS

| 996217 | 8/1976 | Canada ..................................... 364/120 |
| 52-123254 | 10/1977 | Japan ....................................· 364/120 |

Primary Examiner—Joseph F. Ruggiero
Attorney, Agent, or Firm—Cushman, Darby & Cushman

[57] ABSTRACT

There is provided a process control system having a deviation circuit for calculating a deviation of the process variable representing a state of a process to be controlled from the set-point value. And there is provided a process control system further including a differential circuit for differentiating a deviation, a controller for estimating a trend of a process on the basis of the two pieces of information and determining a proper controlling amount of the process variable in accordance with the process trend estimated.

11 Claims, 7 Drawing Figures

PROCESS CONTROL SYSTEM

BACKGROUND OF THE INVENTION

The present invention relates to a process control system with a means for supervising a variation of a process variable representing a state of a process to be controlled.

Conventional process control systems have used a process indicating meter in which process variables, representing a current state of a process which come from sensors provided at the respective portions of a system to be process-controlled, for the purpose of process supervising and the set-point values of the process variables, are indicated on a scale to check to see whether the process variables fall within a tolerable range. Another example uses a cathode ray tube (CRT), in which a simulative chart is depicted on the screen, with marks indicating a tolerable range. In another example for a number of control loops, a tolerable deviation range is covered with a green band and a red pointer is used for indicating a process variable. In this example, when the pointer moves out of the green band, this state is markedly observed. These process supervising methods, however, merely provide information whether a deviation amount of each process variable from its set-point value is within a tolerable range or not. For this reason, when a process variable, which is a controlled variable, is in the tolerable deviation range, an operator can not know whether the process variable will go out of the tolerable deviation range after a short time, similarly, when it is outside the tolerable deviation range, he can not know whether it will enter the tolerable range after a while. When positively knowing the trend of such a process variable, he must carefully observe the supervisory apparatus for each control loop. For this reason, the tolerable deviation range is set up strictly so that an excessive deviation of the process variable, which is more important, is passed over frequently.

Also in the process control, an indicating controller such as a PID indicating controller is provided and the process control is automatically carried out without manual operation. When the process control starts or stops, controlling instruments or the process are abnormal, or when it is desired to settle a process variable to a set-point value in the shortest time, an operator directly determines a controlling amount to control the process. Specifically, the operator performs the process control by determining the controlling amount while referring to the position or the movement of a pointer of the indicating controller, which indicates a process variable, or a trend record of the process variable by a trend recorder.

A deviation quantity between a process variable and its set-point value, which is one of the factors to determine the controlling amount in the process control is displayed on an indicator in the form of a bar length. Accordingly, the operator can read easily and accurately the process variable indicated by the indicator. In controlling the process in a transient condition, a deviation quantity and the differential value of the process variable representing a change state of the process, are needed for the factors to determine the controlling amount. By convention, the operator empirically determines the differential value from a motion of the pointer. For this, the change state of the process variable is poor in preciseness and accuracy. The control accuracy depends largely on individual operators and the controlling time differs for each operating even by the same operator. This encumbers a standardized and systemized process control, and necessitates a skill for the process control.

With an intention of solving this problem, a signal display unit was proposed in which a present value of the process variable and its differential value are displayed as phase points. In the display unit, however, a set-point value and a deviation value between the present value and the set-point value are not displayed, although the differential value is displayed. Therefore, an operator can not directly judge whether the process variable is approaching to or is departing from the set-point value. Accordingly, he often makes an error of the control direction. Moreover, the deviation quantity for determining the controlling amount is not indicated so that it is very difficult to set a process variable to a set-point value.

As described above, a serious problem of the conventional process control system is that, when a process variable is so controlled as to make it coincide with a set-point value, a change trend of process can not correctly be grasped.

SUMMARY OF THE INVENTION

Accordingly, an object of the present invention is to provide a process control system with a process supervising means which can effect a uniform and correct process control.

Another object of the present invention is to provide a process supervising means for a process control system which can indicate not only a deviation quantity of a process variable from a set-point value but also the differential value of the deviation quantity for indicating a change trend of the process variable with respect to the set-point value.

In a process control system according to the invention, a deviation quantity which is a difference between a process variable and the set-point value thereof and a differential value of the deviation quantity are displayed as phase points on a phase plane of a CRT screen, for example. Seeing the phase points, an operator can anticipate a change trend of a process variable thereby to select an optimum controlling amount. When the process dynamic characteristic is expressed by a transfer function of second order, an automatic control is possible under a control method based on the maximum principle of an optimum control theory. Since the deviation quantity and differential value are derived in the process control system according to the invention, a Liapunov function resulting from the orthogonal transformation of a coodinate system representing these values, is available for the phase plane, thereby to secure a sure stability criterion.

Other objects and features of the invention will be apparent from the following description taken in connection with the accompanying drawings, in which:

DESCRIPTION OF THE PREFERRED EMBODIMENT

Figure 1:
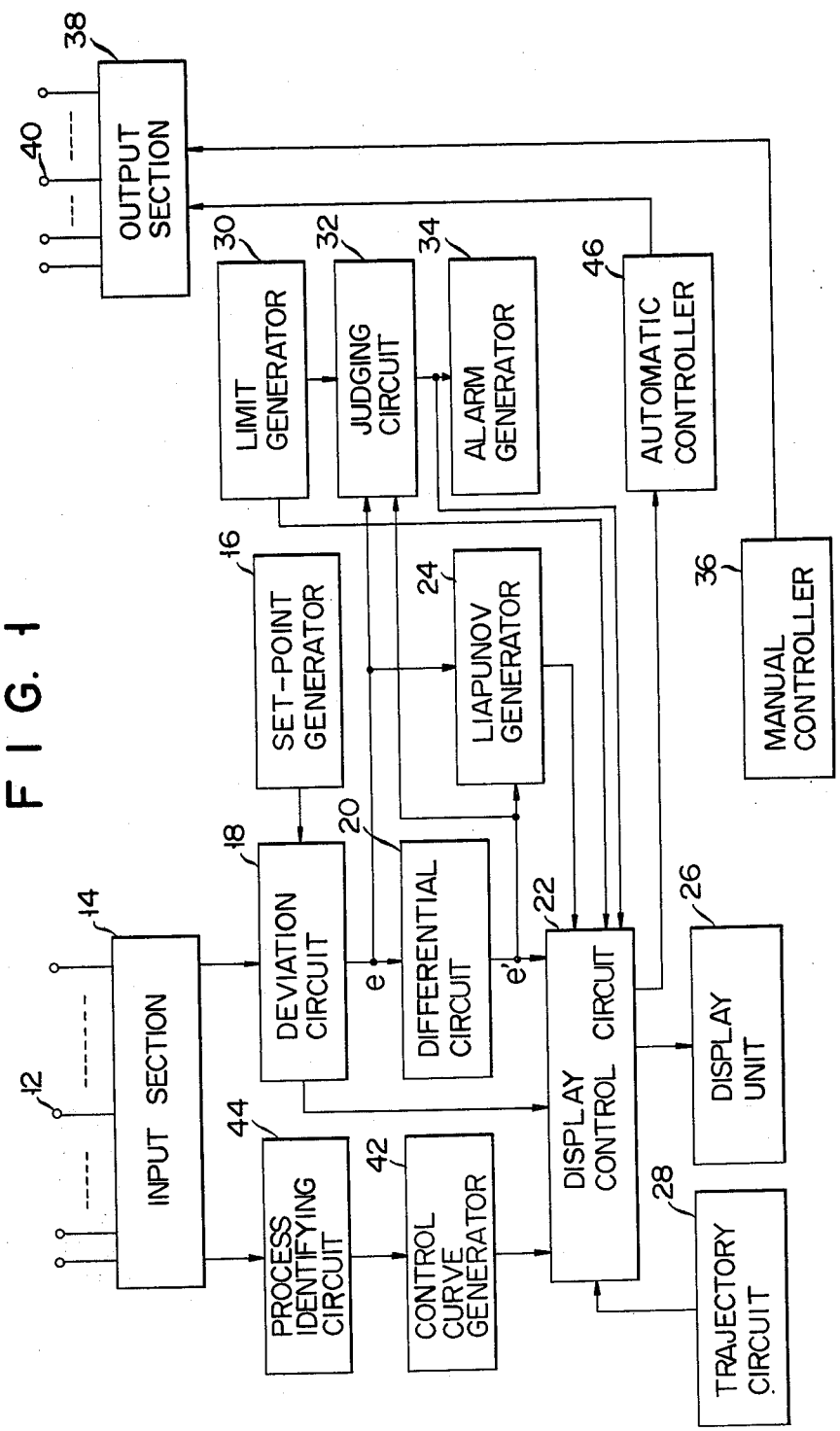
FIG. 1 shows a block diagram of an embodiment of a process control system according to the invention.
Figure 2:
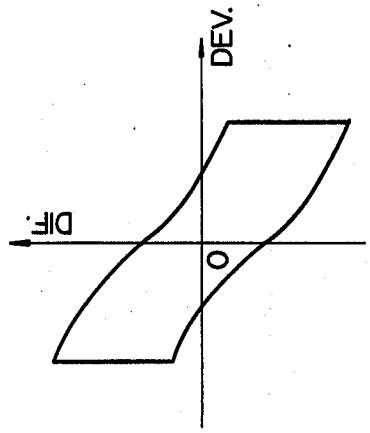
FIG. 2 is a diagram useful in explaining a phase point displayed on a phase plane of a display unit.
Figure 3:
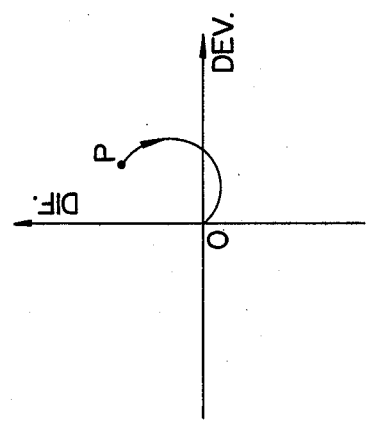
FIG. 3 shows a diagram for explaining a trajectory traced by a phase point displayed on the phase plane of the display unit.
Figure 4:
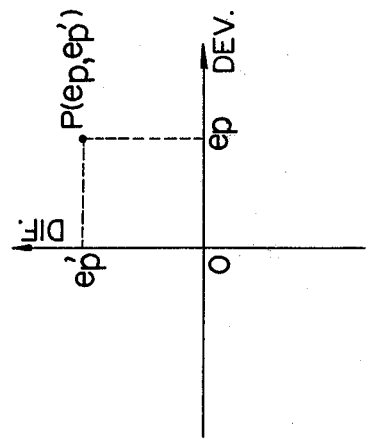
FIG. 4 shows a tolerable deviation range of a process variable displayed on the phase plane of the display unit.

A preferred embodiment of a process control according to the invention will be described with reference to the accompanying drawings. Circuit blocks and the like used in the embodiment to be given are all known ones. Reference is first made to FIG. 1 illustrating a block diagram of process control system which is an embodiment of the invention. Process variables of a controlled process such as temperature, pressure, flow rate, liquid level, concentrations of components and the like are detected by detecting terminals 12 provided on the system to be process-controlled. The process variables detected are loaded periodically or continuously into an input section 14 and these are used as input signals to the process control system. Set-point values are preset in the set-point generator 16, and each input signal and the corresponding set-point value are compared in a deviation circuit 18 so that a deviation quantity e which is a difference therebetween, is produced. The deviation quantity e is differentiated with respect to time by a differential circuit 20 so that a differential value e' is formed. The deviation quantity e and the differential value e', which are thus formed, are loaded into a display control circuit 22 where these are converted into date (for example, e is represented by an abscissa and e' by an ordinate) representing phase points on a phase plane. The data and the coordinate information are both delivered to a display unit 26 such as a CRT where those are displayed on a phase plane, as shown in FIG. 2. The deviation quantity e and the differential value e' are also applied to a Liapunov generator 24 and then are transferred as variables featured by the Liapunov function to a display control circuit 22 whereby those are displayed on the phase plane, with respect to given axes. The set-point generator 16 may be a known device of this kind, and the deviation circuit 18 may be a well known comparator. The differential circuit 20 may also be a well known differential circuit. The display control circuit 22 and the display unit 26 are well known and may include, for example, a CRT display unit. In FIG. 2, a phase point of a process variable is depicted on a phase plane with an abscissa representing a deviation quantity e and with an ordinate representing the differential value thereof. If the phase point is now located at a position P, the deviation quantity and the differential value at this time are $e_p$ and $e_p'$. The process control system of this example not only displays a process state (a deviation amount) as a mere phase point on the phase plane, but also displays a trajectory indicating a time lapse of the phase point. The latter function is effected by a trajectory circuit 28 provided connecting to the display control circuit 22. The display control circuit 22 has a function to control the display of the phase point and the trajectory. When the trajectory circuit 28 is turned to a trajectory designation, the display unit 26 can depict a trajectory as a phase point trace with the lapse of time, as shown in FIG. 3, because the display control circuit 22 has stored past data. A limit generator 30, for setting a tolerable range of deviation of a process variable from the set-point value, traces a tolerable deviation range and coordinates axes as well on the display unit 26, as shown in FIG. 4, through the display control circuit 22. The limit generator 30 is a known function generator for generating a desired differential value corresponding to a deviation value. When a phase point falls within an area defined by two parallel arranged curves in FIG. 4, these lie within the tolerable range. A judging circuit 32, which may be a conventional comparator, for judging whether a phase point is within the tolerable range or not, is connected in receiving relation to the limit generator 30 and to the deviation circuit 18. When the phase point falls outside the tolerable range, an alarm generator 34 connected in receiving relation to the judging circuit 32 generates an alarm signal. In this case, the judging circuit 32 issues a command for change of the color or the shape of the phase point display in order that trouble of a process state is conspicuously displayed.

A manual controller 36 is provided near the display unit 26. The manual controller 36 is used to manually control the process to be supervised and controlled when the process is started, stopped or in an emergency condition. At this time, an operator, while observing the phase point or the trajectory of the phase point on the display unit 26, controls a process variable by manual controller 36 to drive operating terminals 40 such as valves through an output section 38.

The manual controller 36 may be individual units provided in one to one relation for the corresponding operating terminals. When n phase points are simultaneously displayed on a single phase plane of the display unit 26, the manual controller 36 may be a single unit provided in 1 to n relation for the operating terminals 40. In the latter case, a desired operating terminal is selected by the output section 38 in order that a controlling signal is transferred to the operating terminal 40, i.e. corresponding to the phase point to currently be noticed.

Figure 5:
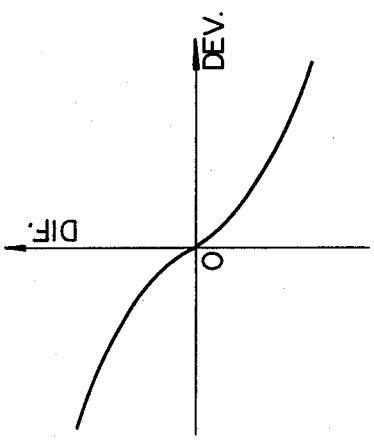
FIG. 5 shows a control switching curve on the phase plane of the display unit.

A control switching curve generator 42 is further provided to facilitate an optimizing control based on the process information on the phase plane. The generator 42 previously stores dynamic characteristic data such as time lag constant, gain, inertia of the process and generates the data representing a control switching curve on the basis of those data. A control switching curve and the coordinate axes are concurrently displayed on a phase plane of the display unit 26, as shown in FIG. 5, through the display control circuit 26. A process identifying circuit 44 is additionally provided which identifies a process dynamic characteristic on the basis of the process variables coming through the input section 14 from the detecting terminals 12 and modifies a process dynamic characteristic data stored in the curve generator 42, depending on the results of the identification. To this end, the curve generator 42 generates a control switching curve matched to a process state at that time. This curve generated is displayed by the display unit 26. The curve generator 42 and the process identifying circuit 44 are well known circuits in this example. An automatic controller 46 coupled with the display control circuit 22 judges which regions on the phase plane divided by the control switching curve has a phase point and determines a proper controlling amount. The automatic controller 46 automatically selects either the maximum or minimum controlling amount to effect the Bang-Bang control based on the maximum principle of the optimizing control theory and produces controlling signals for driving the operating terminals 40 through the output section 38. In this manner, the automatic controller exceecutes an automatic control of the process. In this case, the display unit 26 is used as a means for monitoring the process.

While the example thus far described relates to one control loop (one process variable), the invention is applicable for a plurality of processes. For example, the operating terminals 40 are under control of time division or the controllers may be provided for every operating terminal. A plurality of phase points for the plurality of control loop or trajectories of the phase points having various shapes or colors may also be simultaneously displayed on a phase plane, in addition to a single phase point or the trajectories thereof of a single phase loop. Further, the display unit 26 is not limited to a single unit for displaying a single phase plane. The display area of a single display unit may be divided into a plurality of sectional areas and a plurality of phase planes may be displayed on the corresponding sectional areas. Additionally, a plurality of such display units with segmental display areas may also be used. The display unit 26 is not limited to the one exclusively used for the phase plane display but may be the one available for other uses. A CRT display unit, an X-Y plotter or other display means capable of displaying two-dimensional planes may be used for the display unit 26 of the present invention.

The supervising operation of the process control system thus constructed will be described below. In the process control, it is very important to know a deviation amount of a process variable from the set-point value, which is a controlled variable at the present time point, and a change of the process variable, in order to determine a proper controlling amount. The process control system according to the present invention enables a deviation quantity and its differential value to be simultaneously and directly displayed. Accordingly, the correct and qualitative data concerning a trend of process can be obtained simultaneously.

Explanation will be given how to anticipate a process change from phase points display on a phase plane shown in FIG. 6. Assume now that a tolerable deviation range of a conventional process controller is $\pm \Delta e$ the area of it on the phase plane is a band laying between two dotted lines representing $e = \Delta e$ and $e = -\Delta e$ in FIG. 6. In a conventional supervising method, when the phase points lay in the band area, it is judged that the process is correct and no further control is done.

However, when employed with a phase plane display of a deviation quantity and the differential value thereof, an abnormality in the process can be detected even if the phase point is located in the tolerable deviation range. When a phase point is located at a point $P_1$ in the first quadrant or at a point $P_3$ in the third quadrant, for example, the situation of the process at the present time is judged so that, although the process variable falls within the tolerable deviation range, it will go out of the tolerable range in a short time because the differential value of the process variable is large. Upon this, an operator can accordingly take some proper measure for such a situation. When the phase point is located at a point $P_2$ in the second quadrant or at a point $P_4$ in the fourth quadrant, the judgment is such that the phase point is outside the tolerable deviation range but it will enter the tolerable range soon. In this case, an operator must take no further step of process control since the process will automatically restore to its normal state.

In the case of a plurality of control loops, if the phase points are at points $P_4$ and $P_4'$ in the fourth quadrant, for example, the deviation quantity of $P_4$ is larger than that of $P_4'$ but the absolute differential value of the deviation quantity of $P_4$ is large and therefore a strong restoring force will force the large deviation quantity of $P_4$ to decrease rapidly. On the other hand, the rate of change of deviation of phase point $P_4'$ is small. Therefore, it takes a long time for the phase point to enter the tolerable range. In order to cause the phase point to enter the tolerable range rapidly, some countermeasure must be taken. Similarly, when the phase point is located at points $P_1$ and $P_1'$ in the first quadrant, the phase point $P_1$ is within the tolerable range but the phase point $P_1'$ outside the tolerable range. However, it is anticipated that the deviation quantity of the point $P_1$ will rapidly increase. Therefore, some control measure must be taken for the point $P_1$ earlier than for the phase point $P_1'$.

In the conventional process indicator, even if the deviation quantity is zero, it merely indicates that the phase point lies on the ordinate axis $e = 0$ on the phase plane. When the phase point lies on the ordinate axis other than the origin, the deviation rapidly grows, that is to say, the process is not yet settled. Therefore, some additional control measure must be taken so as to make the phase point coincide with the origin.

As described above, when the process control system according to the invention is used, an operator can grasp qualitatively the deviation quantity and the differential value thereof so that he can supervise more properly the process and judge correct controlling amount. In increasing the deviation quantity, the operator can rapidly take a countermeasure of control, while, in decreasing the deviation quantity, he must take no countermeasure since the process automatically restores to its normal state.

Figure 6:
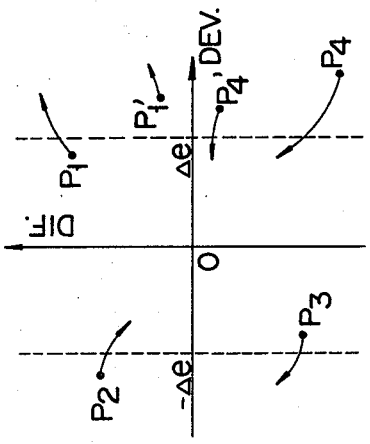
FIG. 6 shows a graph for illustrating a process control according to the invention in which a process is anticipated by displaying phase points on the phase plane of the display section.

With respect to the tolerable deviation range, two parallel disposed dotted lines shown in FIG. 6 may be substituted by a tolerable deviation area enclosed by a distorted rectangular mark as shown in FIG. 4. In this case, when the phase points are outside the tolerable rectangle, the phase points are colored with a conspicuous color. This facilitates the deviation supervisory of a number of control loops.

As seen from the foregoing, when using the process control system according to the invention, an operator can know many pieces of important information, which can not be obtained by the conventional deviation display method. As a result, the process control is improved.

The manual control operation of the process control thus far described, which is used when the system to be process-controlled is started, stopped or in an emergency condition, will be described. While seeing the display unit 26, an operator applies a controlling amount to the process so as to set a process variable, which is a controlled variable to a set-point. Through the control by the operator, even if the value of the process variable is coincident with the set-point value, the settlement is not completed until the differential value is also zero. Accordingly, the ooperator must continue the control until the phase point representing the process variable is coincident with the origin. Thus, since a settling condition is displayed with respect to the origin on the phase plane, an operator can effect a manual operation in an easy manner.

by convention, an operator often settles the maximum or the minimum controlling amount which is permitted in the control loop. The process control system of the invention enables a beginner to easily execute such an excellent control. When the dynamic characteristic of the controlled process is expressed by a transfer function of second order or is approximated by the same transfer function, the phase plane is divided by a control switching curve of the dynamic characteristic, as shown in FIG. 5. In order to settle the process for the shortest time (to make the phase point coincide with the origin on the phase plane), the maximum controlling amount which is permitted in the control loop is applied to the process when the phase point is in the lower area in FIG. 5. When the phase point is in the upper area, the minimum controlling amount is applied to the process. In other words, the Bang-Bang control method based on the maximum principle in the optimizing control theory may be employed. The control switching curve may be theoretically calculated if the dynamic characteristic of the process is known. Accordingly, if the control switching curve, together with the coodinate axes the phase plane, is displayed on the display unit 26, as shown in FIG. 5, an operator checks the area with a boundary of the switching curve where the phase point is located and determines the controlling amount on the basis of the result of the check.

As described above, even a beginner can do the process control with a high accuracy, like an expert.

The control switching curve passes through the origin of the phase plane: however, it is impossible to select either the maximum or the minimum controlling amount near the origin. For this, when the phase point reaches the vicinity of the origin, the control method is then switched to a continuous control such as a PID control or the controlling amount is fixed to a value between the maximum and the minimum controlling amount matched to the set-point at the time.

The description above relates to the manual control of the process by an operator. The control by selecting the maximum and the minimum controlling amount may be performed not only manually but also automatically. In the case of the automatic control, the area where the phase point is located is judged by the automatic controller 46 and the controlling amount is determined and is applied to the operating terminals 40. If desired, an operator can monitor the automatic control characteristic by turning the phase point/trajectory switch circuit 28 to the trajectory side and observing the trajectory of the phase point P displayed on the display unit as shown in FIG. 3. In the controlling amount automatic judging circuit 46, the deviation amount e of a phase point representing a deviation state at that time and a differential value e' of the deviation quantity e are applied to a function representing the manipulated variable switch curve. On the basis of a sign, i.e. positive or negative, of the functional value, it is judged which of the regions divided by the control switching curve is where the phase point lies.

Further, such automatic control is applicable for a case where the dynamic characteristic of the process varies and is limited to the case of the constant dynamic characteristic.

For example, when the process dynamic characteristic varies depending on the set-point selected, the control switching curve generator 42, which has previously stored several kinds of switching curves, produces a control switching curve most suitable for that situation, which is selected by the process identifying circuit 44. When a change of the process characteristic is detected as a change of the parameter in the transfer function of the process characteristic, the process dynamic characteristic identifying circuit 44 detects it and, on the basis of the detected value, modifies the parameter in the control switching curve stored in the control switching curve generator 42 and produces a control switching curve corresponding to the process characteristic at that time.

Figure 7:
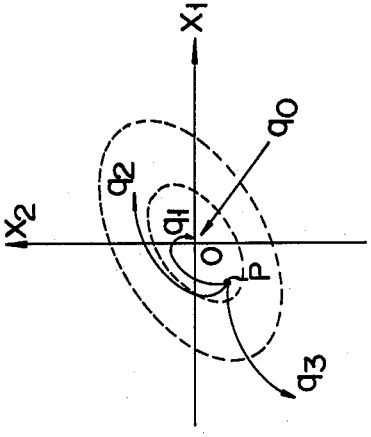
FIG. 7 shows a graph for illustrating a Liapunov stability criterion on the phase plane of the display section.

As described above, the display unit of the process control according to the invention displays a phase plane involving a deviation quantity between a process variable as a controlled variable and a set-point value, and a differential value thereof. Further, it can display a phase plane for Liapunov stability criterion by using the Liapunov generator 24. The Liapunov stability criterion will be described referring to FIG. 7. The phase plane is defined by coordinate axes $x_1$ and $x_2$ which is obtained by orthogonal-transforming the coordinate system of the deviation quantity of the process variable and the differential value of the deviation variable. In the phase plane representation, when the phase point P traces a trajectory indicated by $q_1$, it is judged as "asymptotically stable". When the trajectory traced by the phase point P is as indicated by $q_2$, the judgement is "stable". In the case of a locus $q_3$, the judgement is "instable". Accordingly, the process may be supervised also in the stability. Through this supervising, the stability criterion is obtained to control an unstable process so as to be stable. The instable process may be optimized in a manner that the trajectory of the phase point crosses rectangularly a contour line, as indicated by dotted lines, of a positive definite by the Liapnov stability criterion, as shown $q_0$.

As described above, in the process control system according to the invention, a deviation quantity at present time and a differential value thereof are displayed on a phase plane for displaying a deviation signal between a process variable which is a controlled variable and a set-point value, and a differential signal of the deviation signal. Accordingly, by observing the quadrants on the plane, an operator can directly supervise a stability of the control and can easily make an estimation of control to be made. Additionally, a control system using various kinds of functions and the ON-OFF control is applicable to the process control system of the invention. The process control system of the invention improves the efficiency and the stability of process control.

What is claimed is:

1. A process monitoring system comprising:
   set-point setting means for setting a set-point of a process variable representing a state of a process to be controlled;
   deviation calculation means for calculating a deviation of the process variable from said set-point and producing a deviation signal;
   differentiating means for differentiating said deviation signal and producing a differential signal;
   display control means for converting said deviation signal in real time and said differential signal thereof into a phase signal representing a position, which also represents the present deviation signal and the differential signal thereof, on a phase plane formed on the basis of said deviation signal and said differential signal;

display means for displaying said phase signal; and means for displaying a control curve on said display means, the relative location of said control curve and said position represented by said phase signal indicating to an operator whether a controlling amount should be changed between first and second values.

2. A process monitoring system according to claim 1, in which said display control means is provided with a phase variable operating/generating means for Liapunov stability criterion for orthogonal-transforming said deviation signal and said differential signal into a Liapunov phase signal.

3. A process monitoring system according to claim 1, in which said display control means is provided with a phase point/trajectory indication switch means for displaying said phase signal as a phase point or as a trajectory on said display means.

4. A process monitoring system according to claim 1, in which said display control means includes tolerable deviation range setting means for displaying a tolerable deviation range on said display means and tolerable deviation range judging means for displaying an abnormal deviation on said display means when a deviation of the process variable is abnormal.

5. A process control system comprising:

set-point setting means for setting a set-point of a process variable representing a state of process to be controlled;

deviation calculation means for calculating a deviation of the process variable from said set-point and producing a deviation signal;

differentiating means for differentiating said deviation signal and producing a differential signal;

display control means for converting said deviation signal in real time and said differential signal into a phase signal representing a position, which also represents the present deviation signal and the differential signal thereof, on a phase plane formed on the basis of said deviation signal and said differential signal;

display means for displaying said phase signal; and control means for automatically changing a controlling amount between first and second values to change the process variable to stabilize the system according to said phase signal representing a position on the phase plane.

6. A process control system according to claim 5, in which said display control means is provided with a phase variable operating/generating means for Liapunov stability criterion for orthogonal-forming said deviation signal and said differential signal into a Liapunov phase signal.

7. A process control system according to claim 5, in which said display control means is provided with a phase point/trajectory indication switch means for displaying said phase signal as a phase point or as a trajectory on said display means.

8. A process control system according to claim 5, in which said display control means includes tolerable deviation range setting means for displaying a tolerable deviation range on said display means and tolerable deviation range judging means for displaying an abnormal deviation on said display means when a deviation of the process variable is abnormal.

9. A process control system according to claim 5, in which said display control means includes a control switching curve generating means.

10. A process control system according to claim 9, in which said control switching curve generating means includes process dynamic characteristic identifying means for identifying a process dynamic characteristic in accordance with a process variable.

11. A process monitoring system according to claim 1 or 5, wherein said display control means includes tolerable differential signal range setting means for displaying a tolerable differential deviation range on said display means and tolerable differential deviation range judging means for displaying an abnormal differential deviation on said display means when a differential deviation of the process variable is abnormal.

* * * * *